(12) United States Patent
McDonald et al.

(10) Patent No.: US 8,562,623 B2
(45) Date of Patent: Oct. 22, 2013

(54) VAGINAL OCCLUSION DEVICE

(76) Inventors: Ross Alan McDonald, Mesa, AZ (US);
Laura McDonald, Mesa, AZ (US)

( * ) Notice: Subject to any disclaimer, the term of this patent is extended or adjusted under 35 U.S.C. 154(b) by 227 days.

(21) Appl. No.: 13/024,106

(22) Filed: Feb. 9, 2011

(65) Prior Publication Data
US 2012/0203244 A1 Aug. 9, 2012

(51) Int. Cl.
*A61B 17/42* (2006.01)
(52) U.S. Cl.
USPC .......................................... 606/119
(58) Field of Classification Search
USPC ............. 600/38; 604/279; 606/119, 191, 193, 606/197
See application file for complete search history.

(56) References Cited

U.S. PATENT DOCUMENTS

| | | | | |
|---|---|---|---|---|
| 3,996,930 | A * | 12/1976 | Sekulich | 601/137 |
| 4,509,504 | A | 4/1985 | Brundin | |
| 4,994,069 | A | 2/1991 | Ritchart | |
| 5,540,658 | A | 7/1996 | Evans | |
| 5,643,311 | A * | 7/1997 | Smith et al. | 606/193 |
| 5,674,239 | A * | 10/1997 | Zadini et al. | 606/193 |
| 5,840,077 | A | 11/1998 | Rowden | |
| 5,853,362 | A * | 12/1998 | Jacobs | 600/38 |
| 6,174,317 | B1 | 1/2001 | Engman | |
| 6,602,251 | B2 | 8/2003 | Burbank | |
| 6,958,069 | B2 | 10/2005 | Shipp | |
| 7,052,454 | B2 | 5/2006 | Taylor | |
| 7,220,259 | B2 | 5/2007 | Harrington | |
| 7,223,279 | B2 | 5/2007 | Burbank | |
| 7,398,780 | B2 | 7/2008 | Callister | |
| 7,404,821 | B2 | 7/2008 | Burbank | |
| 7,572,274 | B2 | 8/2009 | Yassinzadeh | |
| 2004/0230093 | A1 * | 11/2004 | Marshall | 600/38 |
| 2005/0107818 | A1 | 5/2005 | Valtchev | |
| 2007/0244538 | A1 | 10/2007 | Eder | |
| 2008/0009775 | A1 * | 1/2008 | Murison | 601/46 |
| 2010/0180422 | A1 * | 7/2010 | Valtchev | 29/428 |
| 2010/0312199 | A1 * | 12/2010 | Lu | 604/279 |
| 2011/0021870 | A1 * | 1/2011 | Lee | 600/38 |
| 2012/0065601 | A1 * | 3/2012 | Gubachy et al. | 604/294 |

* cited by examiner

*Primary Examiner* — Ryan Severson
*Assistant Examiner* — Ashley Fishback
(74) *Attorney, Agent, or Firm* — Thomas W. Galvani, P.C.; Thomas W. Galvani

(57) ABSTRACT

A vaginal occlusion device that prevents the leak of gas out of the vaginal cavity during a laparoscopic surgery. The vaginal occlusion device includes a shaft with a handle attached to one end and a round or oval shaped head attached to the other end. The head is adapted to be inserted into a vagina.

18 Claims, 2 Drawing Sheets

VAGINAL OCCLUSION DEVICE

BACKGROUND OF THE INVENTION

The present invention generally relates to a minimally invasive surgical device. More particularly, the present invention relates to a vaginal occlusion device. In recent years, laproscopic surgery has become a very popular surgical procedure. Laparoscopic surgery may be less invasive than the previous abdominal surgical procedures. Laparoscopic procedures require the abdominal cavity to be filled with gas, forming pneumoperitoneum to allow the surgeon to see and move instruments. Unfortunately, using the vagina as a route for natural orifice extraction following colpotomy, the gas tends to escape through the vaginal opening, making it difficult to maintain surgical exposure during the laparoscopic surgical procedure. In addition, the size of women's vaginal areas varies considerably, necessitating the use of various sized surgical devices.

As can be seen, there is a need for a vaginal device that has universal use and at the same time prevents the leak of gas during laparoscopic surgery.

SUMMARY OF THE INVENTION

In one aspect of the present invention, a vaginal occlusion device having a shaft, including a handle attached to one end, a head attached to the other end, the head has an oval or round shape, and wherein the head is adapted to be inserted into a vagina.

In another aspect of the present invention, a vaginal occlusion device having a one-piece body, including a shaft with a handle attached to one end, a head attached to the other end, the head has an oval or round shape, and the head is adapted to be inserted into a vagina.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a vaginal occlusion device used to maintain pneumoperitoneum following a minimally invasive surgery using the vagina for specimen extraction.

Figure 1:
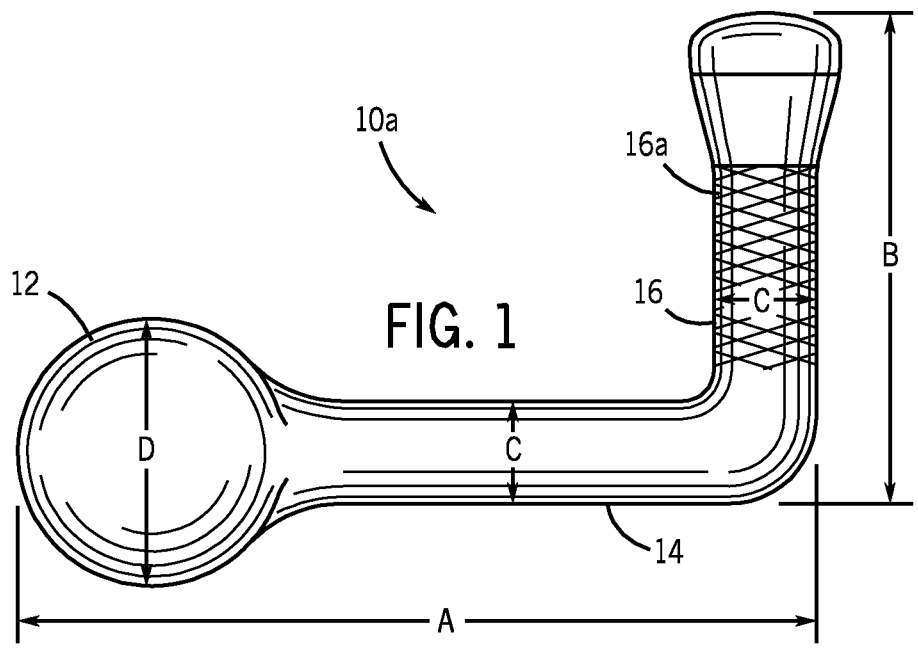
FIG. 1 illustrates a side view of the vaginal occlusion device according to an exemplary embodiment of the present invention.

FIG. 1 illustrates the vaginal occlusion device 10a according to an exemplary embodiment of the present invention. In this embodiment, the vaginal occlusion device 10a may include a shaft 14 having a head 12 at one of its ends and a handle 16 on the other end. The vaginal occlusion device 10 may be manufactured under current biomedical standards.

The shaft 14 may have a length that allows the surgeon to properly place the head 12 inside the vagina 18. In one embodiment, the shaft 14 together with the head 12 may have a length A of approximately 160 mm. The shaft 14 may have a geometrical shape. In one embodiment, the shape of the shaft 14 may be cylindrical, rectangular, or triangular. In one embodiment, the shape of the shaft 14 may be cylindrical with a diameter C of approximately 16 mm. The shaft 14 may be made of a rigid material. In one embodiment, the shaft 14 may be made of a non latex-based material or plastic. The shaft 14 and the handle 16 may be made as a one-piece device.

The handle 16 may allow the surgeon to grip the vaginal occlusion device 10a when being inserted in the vagina 18 that is heavily contaminated with body fluids. The handle 16 may be ergonomically designed to facilitate maintaining the grip of the vaginal occlusion device 10a. The handle 16 may include an anti-slip surface 16a to facilitate the grip of the handle 16.

The handle 16 may have a length B that allows the surgeon to properly control the insertion of the vaginal occlusion device 10a in the vagina 18. In one embodiment, the length B of the handle 16 may be from approximately 120 mm to approximately 140 mm. The handle 16 may have a width C that allows the surgeon to properly control the insertion of the vaginal occlusion device 10a in the vagina 18. In one embodiment, the width C of the handle 16 may be 20 mm. In one embodiment, the handle 14 and the shaft 16 may have the same cross areas. In one embodiment, the handle 14 and the shaft 16 may have different cross areas.

Figure 4:
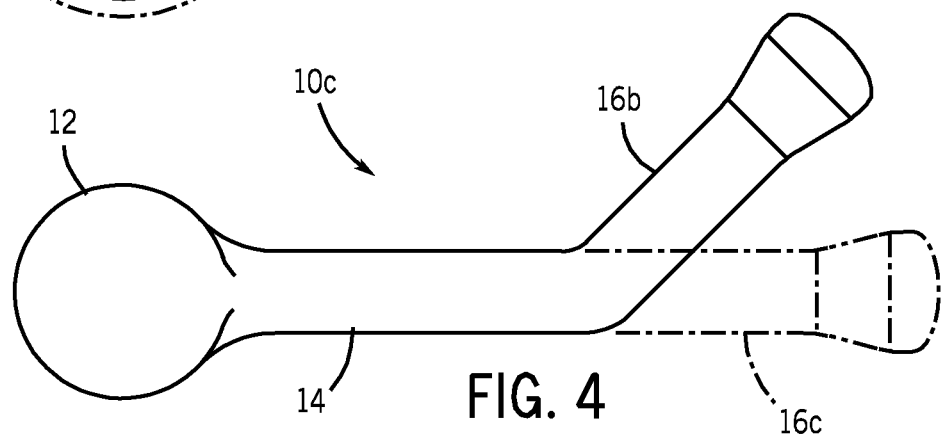
FIG. 4 illustrates a side view of the vaginal occlusion device according to a third exemplary embodiment of the present invention.

The handle 16 may be configured at any angle with respect to the shaft 14 from 0 degrees to 180 degrees. FIG. 4 illustrates a third alternate embodiment of the present invention on which the vaginal occlusion device 10c may include a handle 16b that may be configured at a 45 degree angle with respect to the shaft 14. In addition, FIG. 4 illustrates that the vaginal occlusion device 10c may include a handle 16c that may be configured on the same plane with respect to the shaft 14.

The head 12 may be used to obstruct the vagina 18, preventing the gas from leaking from the abdomen cavity during the laparoscopic procedure. The head 12 may be attached to or form an integral part of the shaft 14 and may not be removable from the shaft 14. The head 12 may be made of a medical-grade rigid material. In one embodiment, the head 12 may be made of medical-grade plastic, non-latex rubber, or silicon. The material of the head 12 may be strong enough to prevent the head 12 from being punctured by a needle 22 on the thread 24 when suturing the vaginal cuff 20 at the end of the vaginal laparoscopic surgery.

The shape of the head 12 may be round or oval to allow the surgeon to block the passage of gas through the vaginal cavity. The round or oval shape of the head 12 may be configured to anatomically match the vaginal cuff area, providing a seal that may prevent the passage of gas from the peritoneal cavity through the vaginal defect. The head 12 may include a smooth surface to protect the interior of the vagina 18. The size of the cross-sectional area D of the head 12 may depend on the female anatomical variances. In one embodiment, the head 12 may have a diameter from 35 mm to 45 mm. In one embodiment, the head 12 may have a diameter of 40 mm. The head 12 may have any color. In one embodiment, the size of the head 12 may be color coded.

Figure 2:
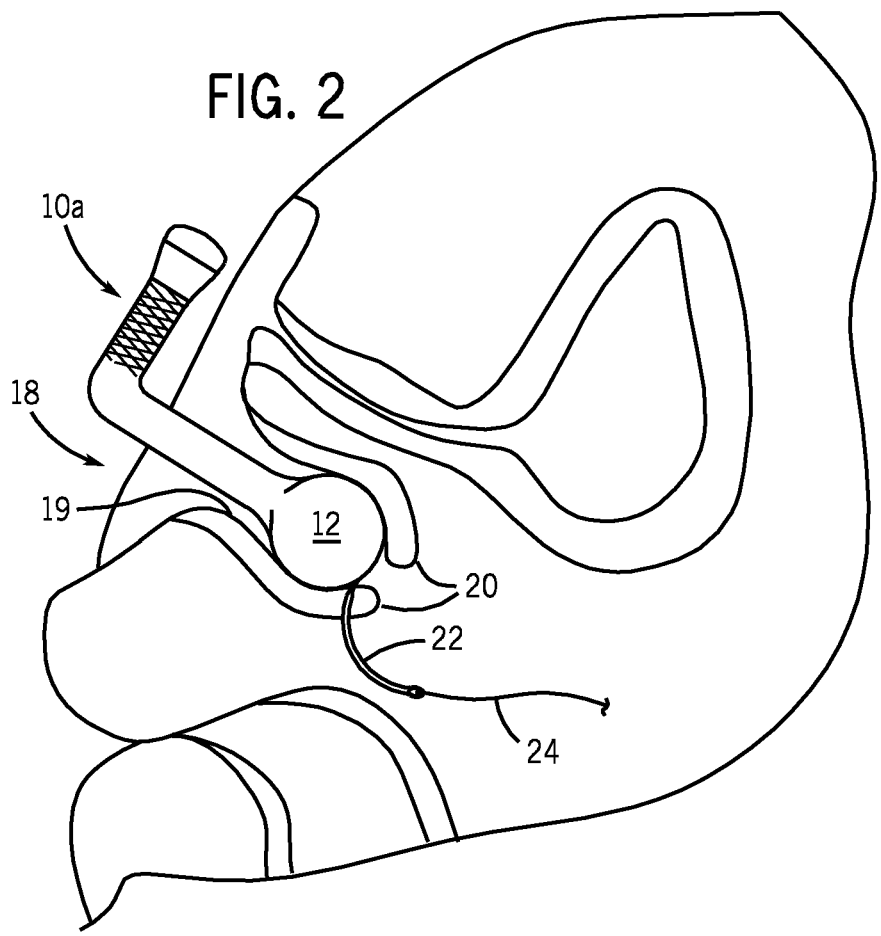
FIG. 2 illustrates a cross-sectional view of a female pelvis showing the vaginal occlusion device of FIG. 1 inserted into the vagina.

FIG. 2 illustrates the vaginal occlusion device 10a that may be inserted into the vagina 18 by the surgeon using the handle 16 to grip and control the angle of insertion. The surgeon may slide the vaginal occlusion device 10a into the vaginal opening 19 of the vagina 18 until the vaginal occlusion device 10a reaches the vaginal cuff 20, blocking the passage of gas from the peritoneal cavity through the vaginal defect.

Figure 3:
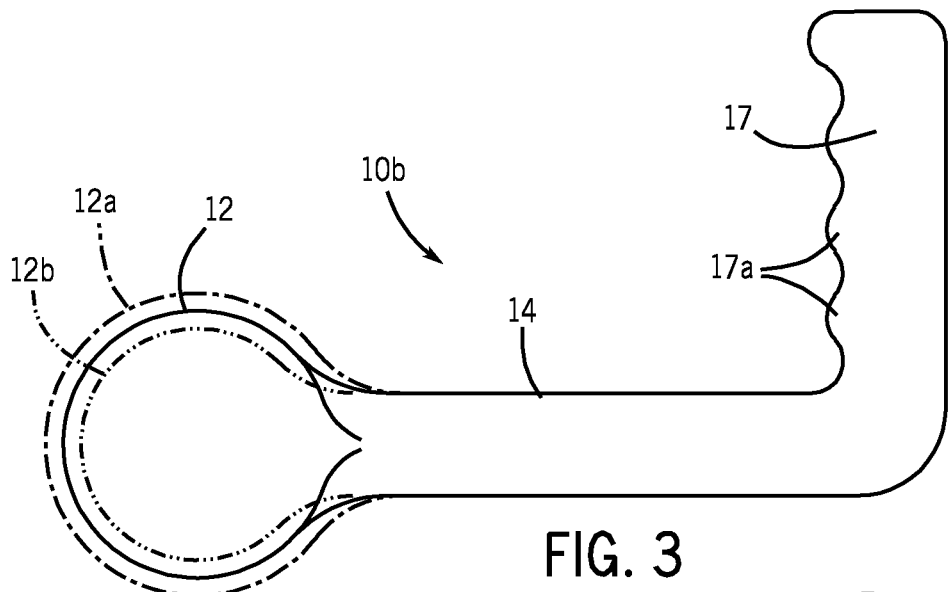
FIG. 3 illustrates a side view of the vaginal occlusion device according to a second exemplary embodiment of the present invention.

FIG. 3 shows a second alternate embodiment of the present invention on which a vaginal surgical device 10b may include a handle 17 having fingered grips 17a. In addition, the FIG. 3 illustrates that the head 12 may be round. The size of the head 12 may vary from a small size rounded shaped head 12b to a large size round shaped head 12a.

Figure 5:
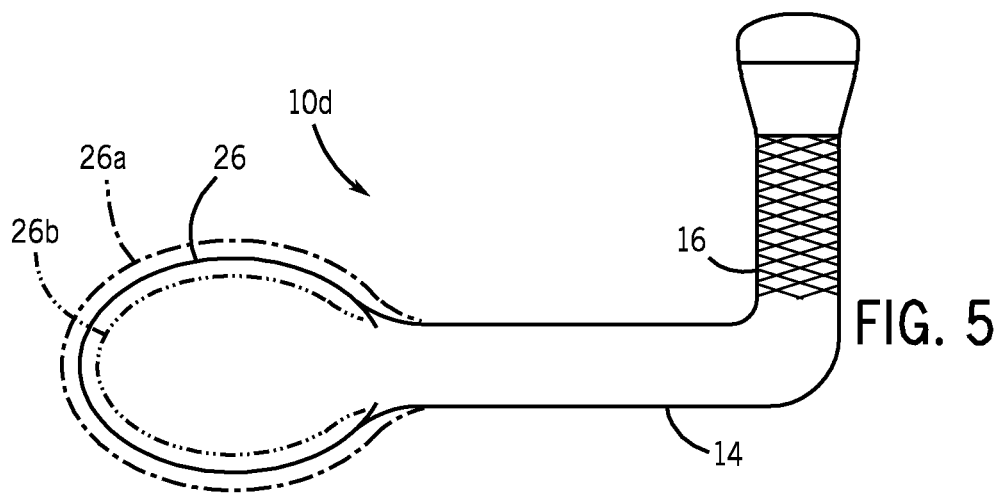
FIG. 5 illustrates a side view of the vaginal occlusion device according to a fourth exemplary embodiment of the present invention.

FIG. 5 illustrates a fourth embodiment of the present invention showing a vaginal occlusion device 10d showing a head 26 having an oval shape. The size of the head 26 may vary from a small size oval shaped head 26b to a large size oval-shaped head 26a. The oval-shaped head 26a may allow for use in other laparoscopic surgical applications.

The vaginal occlusion device 10a-d may be sterile, radio-opaque, and disposable.

The vaginal occlusion device 10a-d may prevent the retention of foreign bodies caught by sutures, such as glove materials or surgical sponges in the vagina 18.

It should be understood, of course, that the foregoing relates to exemplary embodiments of the invention and that modifications may be made without departing from the spirit and scope of the invention as set forth in the following claims.

What is claimed is:

1. A plurality of vaginal occlusion devices, each device for maintaining pneumoperitoneum of a peritoneal cavity in laproscopic surgery, each device comprising:
   a shaft having a first end and a second end;
   a handle attached to the first end of the shaft;
   a head attached to the second end of the shaft, wherein the head has an oval or round shape;
   the head is adapted to be inserted into a vagina in an inserted condition of the device;
   the head of each device has a respective size different from the sizes of the heads of the other devices;
   the head of each device carries a respective color different from the colors of the heads of the other devices;
   the color of the head of each device corresponds to the respective size of the head; and
   in the inserted condition of one of the devices, the head of the device occludes a vaginal cuff to block passage of gas from the peritoneal cavity through a vaginal cavity so as to maintain pneumoperitoneum.

2. The vaginal occlusion device according to claim 1, wherein the head is made of a rigid material.

3. The vaginal occlusion device according to claim 1, wherein the handle and shaft are made of a non latex-based material.

4. The vaginal occlusion device according to claim 1, wherein the handle includes at least one of a non-slip surface and finger grips.

5. The vaginal occlusion device according to claim 1, wherein the handle is placed at a 0 to 180 degree angle with the shaft.

6. The vaginal occlusion device according to claim 1, wherein the head has a smooth surface.

7. The vaginal occlusion device according to claim 1, wherein the shaft, handle, and head comprise a one-piece body.

8. The vaginal occlusion device according to claim 7, wherein the one-piece body is rigid.

9. The vaginal occlusion device according to claim 1, wherein the device is constructed of a radio-opaque material.

10. The vaginal occlusion device according to claim 1, wherein the head of the device is constructed of a puncture-resistant material.

11. The vaginal occlusion device according to claim 1, wherein the head of the device is constructed of a needle-impermeable material providing a hard surface adapted to prevent the head of the device from being sutured.

12. The vaginal occlusion device according to claim 1, wherein in the inserted condition of the device, the head of the device is stationary with respect to the vaginal cuff.

13. The vaginal occlusion device according to claim 1, wherein:
   the shaft has a width; and
   the head has a width about twice as great as the width of the shaft.

14. A plurality of vaginal occlusion devices, each device for maintaining pneumoperitoneum in laproscopic surgery of a peritoneal cavity, each device comprising:
   a rigid shaft including an enlarged head and an opposed handle;
   each head having a size different from the sizes of the heads of the other devices;
   the head of each device carries a respective color different from the colors of the heads of the other devices;
   the color of the head of each device corresponds to the respective size of the head; and
   an inserted condition of the shaft of one of the devices in a vagina;
   wherein in the inserted condition of the shaft, the shaft is inserted into the vagina against a vaginal cuff of the vagina, providing a seal against the vaginal cuff preventing passage of gas from the peritoneal cavity through the vagina.

15. The vaginal occlusion device according to claim 14, wherein the device is constructed of a radio-opaque material.

16. The vaginal occlusion device according to claim 14, wherein the head of the device is constructed of a needle-impermeable material providing a hard surface adapted to prevent the head of the from being sutured.

17. The vaginal occlusion device according to claim 14, wherein in the inserted condition of the device, the head of the device is stationary with respect to the vaginal cuff.

18. The vaginal occlusion device of claim 14, wherein:
   the shaft has a width; and
   the head has a width about twice as great as the width of the shaft.

* * * * *